United States Patent [19]

Zama et al.

[11] Patent Number: 5,081,248

[45] Date of Patent: Jan. 14, 1992

[54] PYRIDINE-N-OXIDE DERIVATIVE

[75] Inventors: Yoshiyuki Zama; Takanobu Naitou; Toshiyuki Yamamoto, all of Ohtsu, Japan

[73] Assignee: Kaken Pharmaceutical Co., Ltd., Tokyo, Japan

[21] Appl. No.: 619,993

[22] Filed: Nov. 30, 1990

[30] Foreign Application Priority Data

Dec. 1, 1989 [JP] Japan .................................. 1-312885

[51] Int. Cl.$^5$ .......................................... C07D 213/69
[52] U.S. Cl. ..................................... 546/296; 546/14; 540/217
[58] Field of Search ........................................ 546/296

[56] References Cited

PUBLICATIONS

Greene, Protective Groups in Organic Synthesis, pp. 29, 30, 32–36, 47, 79, 80, 168, 239, 265–266, Wiley-Interscience Pub. (1981).

Klingsberg, Pyridine and Its Derivatives, Part Two, pp. 134–135, (1961).

*Primary Examiner*—Alan L. Rotman
*Attorney, Agent, or Firm*—Oblon, Spivak, McClelland, Maier & Neustadt

[57] ABSTRACT

A pyridine-N-oxide derivative of the formula:

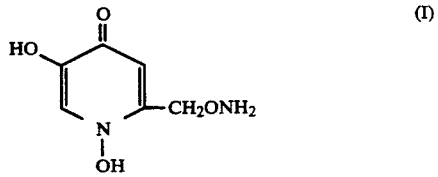

or a salt thereof.

1 Claim, No Drawings

PYRIDINE-N-OXIDE DERIVATIVE

The present invention relates to a novel pyridine-N-oxide derivative. More particularly, it relates to a novel intermediate compound useful for the production of cephalosporin derivatives useful as antibacterial agents.

Heretofore, many synthetic antibacterial agents are known. However, cephalosporin derivatives having a pyridine-N-oxide structure have not yet been practically developed.

The present inventors were successful in preparing cephalosporin compounds showing remarkable antibacterial activities against both gram-positive bacteria and gram negative bacteria, particularly against *Pseudomonas aeruginosa* by introducing a novel substituent at the 7-position of the cephem ring (Japanese Unexamined Patent Publication No. 152386/1988).

Now, the present inventors have discovered a pyridine-N-oxide as a novel intermediate compound useful for the production of such cephalosporin compounds. The present invention has been accomplished on the basis of this discovery.

The present invention provides a novel pyridine-N-oxide derivative of the formula:

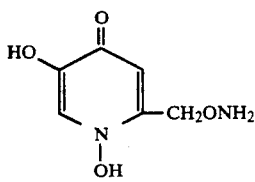
(I)

and a salt thereof. The salt is a salt with a pharmaceutically acceptable non-toxic acid or base. As the salt with an acid, a salt with an inorganic acid such as a hydrogen halide acid (such as hydrochloric acid or hydrobromic acid) or sulfuric acid, or a salt with an organic acid such as fumaric acid or citric acid, may be mentioned. Further, as the salt with a base, a salt with an alkali metal such as sodium or potassium, a salt with ammonia, or a salt with an organic base such as dicyclohexylamine, triethylamine, ethanolamine, ornithine or lysine, may be mentioned.

The compound of the formula (I) of the present invention has keto-form and enol-form tautomers as shown below.

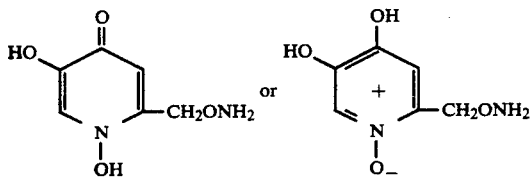

The scope of the present invention includes the above tautomers and a mixture thereof.

The compound of the formula (I) of the present invention can be produced by removing protecting groups $R_1$ and $R_2$ for hydroxyl groups in a compound of the formula:

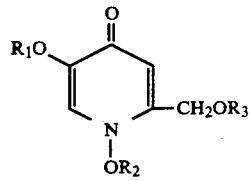
(II)

wherein $R_1$ and $R_2$ independently represent protecting groups for hydroxyl groups, and $R_3$ is an amino group or a phthalimide group, and when $R_3$ is a phthalimide group, removing the phthaloyl group.

With respect to $R_1$ and $R_2$, the protecting group for a hydroxyl group includes, for example, a tri-lower alkylsilyl group such as a trimethylsilyl group, an acyl group such as a formyl group, an acetyl group or a propionyl group, an aralkyl group such as a benzyl group, a p-methoxybenzyl group, a p-nitobenzyl group, a benzhydryl group or a trityl group, a methoxymethyl group, an allyl group and a pyranyl group.

For the removal of protecting groups, protecting groups $R_1$ and $R_2$ in the formula (II) can be removed by usual methods depending upon the nature of the protecting groups. Likewise, in the case where $R_3$ is a phthalimide group, the phthaloyl group is removed.

For example, as methods for removing protecting groups, there may be mentioned a method wherein an acid, for example, an organic acid such as formic acid or trifluoroacetic acid, a hydrogen halide acid such as hydrogen iodide acid, hydrogen bromide acid or hydrogen chloride acid in acetic acid, a sulfonic acid such as methanesulfonic acid in trifluoroacetic acid, or a Lewis acid such as aluminum chloride, aluminum bromide or boron trifluoride in the presence or absence of anisole or thioanisole, is used, a method wherein an alkali such as sodium hydroxide, sodium carbonate, sodium hydrogencarbonate or aqueous ammonia, is used, a method wherein a silane halide such as trimethylsilane iodide is employed, and a method wherein a catalyst for catalytic reduction such as palladium or platinum is used. By the above methods, the reaction is conducted usually within a range of from $-20°$ to $120°$ C. for from 5 minutes to 12 hours, if necessary, with an addition of a suitable solvent.

The compound of the formula (I) of the present invention is useful as an intermediate compound for the production of cephalosporin derivatives useful as antibiotics.

Now, the present invention will be described in further detail with reference to a Reference Example and working Examples. However, it should be understood that the present invention is by no means restricted by such specific Examples.

REFERENCE EXAMPLE

2-Aminooxymethyl-1,5-dibenzhydryloxy-4-pyridone

To 48.2 g (0.1 mol) of 2-phthalimidooxymethyl-1,5-dibenzhydryloxy-4-pyridone, 200 ml of methanol was added. Further, 8.4 g (0.168 mol) of hydrazine hydrate was added thereto at room temperature. The mixture was reacted at room temperature for 5 hours. After completion of the reaction, insoluble matters were removed by filtration. The filtrate was concentrated, and precipitated crystals were collected by filtration. The crystals were dissolved in 200 ml of chloroform, and insoluble matters were removed by filtration. The filtrate was concentrated to dryness, and the product was washed with diethyl ether and dried to obtain 28.4 g of the above identified compound (yield: 83%).

Melting point: 147.5°-148.5° C.

IR(KBr, cm$^{-1}$): 3320, 3240 (-NH), 1620(C=O), 1570, 1540 (C=C)

$^1$H-NMR(DMSO-d$_6$,δ): 7.99(1H,s), 7.45(5H,s), 7.38(5H,s), 6.22(1H,s), 5.25(2H,s), 5.03(2H,s), 4.53(2H,s).

EXAMPLE 1

2-Aminooxymethyl-1,5-dihydroxy-4-pyridone

To 90 g (0.263 mol) of 2-aminooxymethyl 1,5-dibenzhydryloxy-4-pyridone obtained in the above Reference Example, 900 ml of glacial acetic acid and 180 ml of concentrated hydrochloric acid were added. The mixture was reacted at a temperature of from 90° to 100° C. for 7 hours. After completion of the reaction, the reaction solution was concentrated. To the concentrated solution, 600 ml of water and 200 ml of chloroform were added, and the aqueous layer was separated. To the aqueous layer, 4.5 g of active carbon was added, and decoloring carbon treatment was conducted. Then, decoloring carbon was removed by filtration. To the filtrate, an aqueous sodium hydrogencarbonate solution was added to adjust the pH to a level of from 5.2 to 5.5, whereupon precipitated crystals were collected by filtration. The crystals were washed sequentially with water, ethyl alcohol and ethyl ether, followed by drying to obtain 37.9 g (yield: 87.8%) of the above identified compound as a slightly yellowish white product.

Melting point: 185°-190° C. (decomposed)

IR(KBr, cm$^{-1}$): 3320, 3260,(-NH), 1620(C=O)

$^1$H-NMR(CF$_3$COOH+DMSO-d$_6$, δ): 8.30(1H,s), 7.40(1H,s), 5.48(2H,s).

EXAMPLE 2

2-Aminooxymethyl-1,5-dihydroxy-4-pyridone (another method)

To 38.6 g of 2-phthalimidooxymethyl-1,5-dibenzhydryloxy-4-pyridone, 220 ml of glacial acetic acid and 48 ml of concentrated hydrochloric acid were added, and the mixture was reacted at 100° C. for 3 hours. After completion of the reaction, the reaction solution was concentrated. To the concentrated solution, 240 ml of water was added, and insoluble matters were separated by filtration. The insoluble matters were washed with 80 ml of water, and the filtrate and the washing solution were put together. Then, a powder of sodium carbonate was added thereto to adjust the pH to 3.0, whereupon precipitates were collected by filtration. A powder of sodium carbonate was further added to the filtrate to adjust the pH to 5.2, and the mixture was stirred for 2 hours and then left to stand overnight in a refrigerator. Precipitated crystals were collected by filtration, and the crystals were washed with water and then dried to obtain 8.1 g of the above identified compound as a slightly yellowish white product. The IR and NMR spectra of the compound thus obtained, agreed with those obtained in Example 1.

EXAMPLE 3

Preparation of (6R,7R)-7-[(Z)-2-(2-aminothiazol-4-yl)-2-(1,5-dihydroxy-4-pyridon-2-ylmethyoxyimino)acetamide]-3-(1,2,3-thiadiazol-5-ylthiomethyl]-3-cephem-4-carboxylic acid

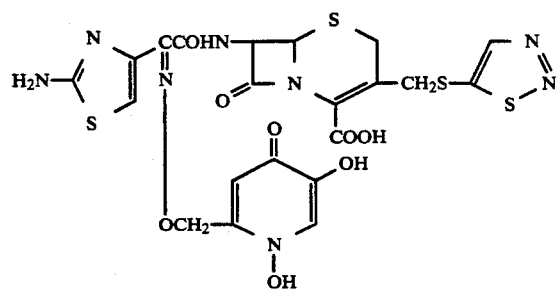

2.2 g of 2-aminooxymethyl-1,5-dihydroxy-4-pyridone obtained in Example 1 and 1.2 ml of concentrated hydrochloric acid were added to 30 ml of a solvent mixture of dimethyl sulfoxide and water (9:1) and stirred at room temperature until they were dissolved. Then, the solution was cooled to 0° C.. To this solution, 5.47 g of (6R,7R)-7-[(Z)-2-(2-aminothiazol-4-yl)-2-oxoacetamide]-3-(1,2,3-thiadiazol-5-ylthiomethyl)-3-cephem-4-carboxylic acid mononitrate was gradually added and stirred until it was dissolved. Then, the solution was left to stand still at 0° C. for 2 days. To this solution, 90 ml of acetone was added, and the mixture was stirred under cooling with ice, whereby crystals of the hydrochloride of the above identified compound precipitated. The crystals were collected by filtration, then suspended in 20 ml of water and dissolved by adjusting the pH to 8 with a saturated sodium hydrogencarbonate aqueous solution. This solution was adjusted to pH 3 with 1N hydrochloric acid, whereupon precipitates were collected by filtration to obtain 4.7 g of the above identified compound.

$^1$H-NMR(DMSO-d$_6$, δ): 3.63 (2H,ABq), 4.25(2H,brs), 5.19(3H,m), 5.82(1H,dd,J=5Hz,8Hz), 6.81(1H,s), 6.84(1H,s), 7.80(1H,s), 8.87(1H,s).

We claim:

1. A pyridine-N-oxide derivative of the formula:

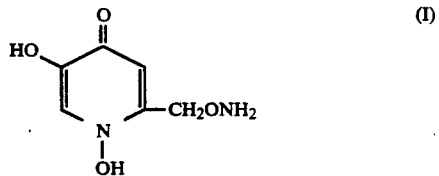

or a salt thereof.

* * * * *